United States Patent [19]

Ghebre-Sellassie et al.

[11] Patent Number: 5,084,287

[45] Date of Patent: Jan. 28, 1992

[54] PHARMACEUTICALLY USEFUL MICROPELLETS WITH A DRUG-COATED CORE AND CONTROLLED-RELEASE POLYMERIC COAT

[75] Inventors: Isaac Ghebre-Sellassie, Stanhope; Uma Iyer, Mendham, both of N.J.

[73] Assignee: Warner-Lambert Company, Morris Plains, N.J.

[21] Appl. No.: 494,206

[22] Filed: Mar. 15, 1990

[51] Int. Cl.$^5$ .................. A61K 9/58; A61K 9/62; A61K 9/16

[52] U.S. Cl. .................. 424/495; 424/494; 424/497; 424/461; 424/462; 514/951

[58] Field of Search ............... 424/489, 490, 495, 494, 424/461; 514/963, 951, 952

[56] References Cited

U.S. PATENT DOCUMENTS

| | | | |
|---|---|---|---|
| 4,508,702 | 4/1985 | Hsiao | 424/19 |
| 4,524,060 | 6/1985 | Mughal et al. | 424/19 |
| 4,587,118 | 5/1986 | Hsiao | 424/19 |
| 4,600,645 | 7/1986 | Ghebre-Sellassie et al. | 428/403 |
| 4,623,588 | 11/1986 | Nuwayser et al. | 424/402.24 |
| 4,786,509 | 11/1988 | Chang et al. | 424/490 |
| 4,800,084 | 1/1989 | Zerbe | 424/495 |
| 4,935,247 | 6/1990 | Marttila et al. | 424/497 |

OTHER PUBLICATIONS

I. Ghebre-Sellassie, Ed., "Pharmaceutical Pelletization Technology", *Drugs and the Pharmaceutical Sciences*, vol. 37, pp. 50-54.

*Primary Examiner*—Thurman K. Page
*Assistant Examiner*—E. Webman
*Attorney, Agent, or Firm*—Ruth H. Newtson

[57] ABSTRACT

A pharmaceutical preparation comprising drug micropellets containing a drug coated on a core material wherein each pellet ranges in size from about 70 microns to 750 microns and wherein each micropellet is coated with a controlled release coating.

4 Claims, No Drawings

PHARMACEUTICALLY USEFUL MICROPELLETS WITH A DRUG-COATED CORE AND CONTROLLED-RELEASE POLYMERIC COAT

FIELD OF INVENTION

This invention relates to compositions which are micropellets of drugs having a functional coating that contributes to the release characteristics of the drug and methods for preparing the drug micropellets.

BACKGROUND OF INVENTION

Micropellets of drugs have been known to the pharmaceutical industry for a long time and began gaining popularity as an oral dosage form as early as the 1950's. The most popular means for forming pellets include the extrusion/spheronization process, the solution/suspension layering process, and the powder layering process. Depending in part on the type of process employed a typical pellet for oral administration ranges in size from 0.5 mm to 1.5 mm. The process employed in the present invention is of the solution/suspension layering type and is unique in that pellets of a size considerably smaller than the typical pellet currently found in industry are formed. The size of the drug micropellets of the present invention renders this drug dosage form more efficacious and easier to administer orally.

INFORMATION DISCLOSURE

U.S. Pat. No. 4,600,645 issued July 15, 1986, teaches coating drug pellets of, e.g., diphenhydramine, with ethylcellulose and applying an overcoat of hydroxypropylmethyl cellulose. The size of the drug pellet is not indicated.

U.S. Pat. No. 4,587,118 issued May 6, 1986, describes micropellets formed by coating sugar seeds (60/80 mesh) with micronized theophylline onto which is sprayed an outer sustained release coating comprising a mixture of ethylcellulose (70-90%) and hydroxypropylcellulose (10-30%). The micropellets are placed in an easily opened capsule so the micropellets may be sprinkled on food.

U.S. Pat. No. 4,508,702 issued Apr. 2, 1985, describes a sustained release formulation comprising aspirin seeds (30 to 60 mesh) coated with a polymeric coating of ethylcellulose and hydroxypropylcellulose in a weight ratio of 2.5:1 to 15:1 and preferably 8:2. The coated aspirin is contained in a capsule or sealed pouch to permit sprinkling of the aspirin on food or beverage.

U.S. Pat. No. 4,786,509 issued Nov. 22, 1988, describes sustained release micropellets formed by coating theophylline in micronized form onto a sugar seed (60-80 mesh) and applying an ethylcellulose coating. The micropellets are placed in capsules then poured from the capsules onto food for oral administration.

U.S. Pat. No. 4,524,060 issued June 18, 1985, describes pellets of indoramin coated with ethylcellulose and a polymer selected from inter alia hydroxypropylmethyl cellulose.

U.S. Pat. No. 4,623,588 issued Nov. 18, 1986, describes micropellets useful for oral or parenteral administration having a size less than 1,000 microns, e.g., 5 to 100 microns wherein the micropellet comprises a composite core of drug and polymer with a coating of same polymer.

SUMMARY OF INVENTION

The present invention provides a pharmaceutical preparation comprising drug micropellets wherein each pellet ranges in size from about 170 microns to 750 microns and wherein each micropellet is coated with a controlled release coating.

The present invention provides an oral dosage preparation of coated drug micropellets wherein the drug component comprises active agents which are typically administered in low dose amounts and includes bronchodilators such as procaterol or theophylline, antihistamines, such as diphenhydramine, and terfenadine, antibiotics, such as doxycycline hyclate, antiinfectives, such as, minocycline HCl, and cardioactive agents, such as, digoxin.

The active ingredients are administered in their usual recommended amounts on an oral basis. For example, procaterol is administered at a daily dose of 100 $\mu$g BID; theophyline at 400 mg; diphenhydramine at 25 mg TID; terfenadine at 60 mg BID, etc. BID means twice a day and TID means three times a day.

As will be apparent from the following the present invention offers several advantages over currently available formulations. The drug particles in the prior art preparations complexed with ion exchange resins are enclosed by a functional membrane. The coated drug micropellet of the present invention is suspended in a vehicle completely devoid of ions. Further the release of drug is triggered when the ingested dose contacts competing ions that displace the bound drug. Also, the release mechanism involves dissociation and diffusion.

DETAILED DESCRIPTION OF INVENTION

The coated micropellets of the present invention are designed to be administered by sprinkling a unit dosage of the active ingredient on food to be eaten or by mixing a unit dosage of the active ingredient in a beverage to be drunk. Although a unit dosage amount of the coated micropellet preparation could be measured from a container containing the preparation for safety and convenience of administering a uniform dosage amount the coated micropellets typically are packaged in an easily opened container such as a sealed pouch or sachet or a capsule which can be opened readily to permit distribution of the unit dosage of drug micropellets to be added to a beverage or food for consumption. Such capsules and pouches are well known to and readily available to the industry for use in packaging the drug preparation.

The drug micropellets of the present invention are formed by layering a solution or suspension of the active ingredient on starter particles, i.e., a core material and then coating the finished micropellet with a functional layer to provide the necessary release characteristics. The starter particles or seeds can be any free flowing nonfriable granular material such as sucrose or lactose or can be crystals of the active ingredient which serve as starter seeds. In addition to the active ingredient or drug the layering formulation may include a binder that promotes adhesion of the drug to the starter seeds, antiadherents that prevent or minimize agglomeration during the layering process, and other ingredients such as surfactants, buffers, coloring, or flavoring agents which may be desirable depending on the physiochemical properties of the active ingredient. The size of the starter particles and the total solids in the layering formulation will determine the size of the finished micropellets.

As indicated above the present invention is particularly unique in the size of the finished coated micropellet formulation. The size of the starter particles may range in size from 10 µ to 500 µ with the preferred range being from 50 µ to 250 µ. The preferred starter seeds are lactose granules or particles of the active ingredient to be formulated, however, other free flowing materials known to the art having the desired shape and surface properties may be employed in practicing the present invention.

The active ingredient is applied by placing the starter particles in a fluid bed apparatus, e.g., a fluid bed bottom spray coater, such as, the Wurster coating apparatus (*Pharmaceutical Pelletization Technology*, (1989) pp. 50-54, ed. Isaac Ghebre-Sellassie, Marcel Dekker, Inc., New York and Basel). A solution or suspension of the active ingredient is sprayed on the fluidizing bed of starter particles until the desired amount of drug loading or layering is achieved. When a suspension of the active ingredient is used in the layering process the active ingredient must be micronized and be of a particle size which is at least ten times smaller than the usual particle or crystal size of the active ingredient.

The layering solution or suspension of active ingredient is formed by dissolving or dispersing the active in distilled water or other pharmaceutically acceptable liquid such as a volatile organic solvent. Antiadherents and binders and other excipients or ingredients as is desirable or appropriate are added to the solution or suspension.

The ratio of active ingredient to starter particle varies according to the unit dosage of drug to be employed and the size of the starting particle. It is apparent that the ratio could vary widely depending on the dosage amount to be employed. For example, it may be desirable or necessary for the finished preparation to consist of a micropellet wherein the active ingredient is layered onto a small number of starter particles having a small diameter or wherein the active ingredient is layered more sparingly onto a higher number of starter particles of the same small or a different size diameter starter particle.

Following formation and drying of the drug micropellet a coating is applied. The nature of the coating varies according to the type of release characteristics desired for the final coated drug pellet formulation.

The coating can be a type which will allow immediate release of the active ingredient into the buccal cavity or the gastric muscosa or the coating can be one which provides a sustained release of the active ingredient wherein the primary release of the active ingredient would occur in the intestinal mucosa. Typical coating materials useful in preparing an immediate release coated micropellet include hydroxypropyl cellulose, hydroxypropylmethyl cellulose polyvinylpyrrolidone. Typical coating materials useful in preparing sustained release or enteric preparations include ethyl cellulose, hydroxypropylmethyl cellulose phthalate, acrylic polymers such as methacrylic acid methyl methacrylate co-polymers, vinylidene chloride-acrylonitrile co-polymers, cellulose acetate butyrate, cellulose triacetate, polyethylene, polypropylene, and other materials well known to one skilled in the art.

The coating material is applied to the drug micropellets in the fluid bed bottom spray coater by having the pellets suspended in an air stream and an organic or aqueous solution of the coating material sprayed onto the micropellets. Once the coating is applied the coated drug micropellets are removed from the fluid bed apparatus and are packaged for use. Any organic base solvent compatible with the coating and which is pharmaceutically acceptable may be used, and illustrative examples of such solvents include lower alcohols such as methanol, ethanol, and isopropyl alcohol, methylene chloride, acetone, chloroform and combinations thereof.

In a preferred embodiment of the present invention, the drug micropellets prepared as described above are overcoated, i.e., have applied thereto a second coating for the purpose of enhancing fluidity and reducing tackiness. The overcoat comprises hydrophilic polymeric materials such as hydroxypropyl cellulose, polyethylene glycol and polyvinylpyrrolidone. A particularly preferred embodiment of the present invention comprises drug micropellets having a first coat of ethyl cellulose and a second coat of hydroxypropylmethyl cellulose. Another particularly preferred embodiment of the present invention is coated drug micropellets wherein the active ingredient is diphenhydramine or procaterol.

As noted above, it may be useful to add binders or antiadherents to the drug solution or suspension in forming the drug micropellets. Typical binders which find use in the present invention include materials having a low molecular weight and low viscosity such as polyvinylpyrrolidone, vinyl, acetate, gelatin, hydroxypropyl cellulose, hydroxypropylmethyl cellulose, sucrose and starch. Illustrative of antiadherents which may be used in the present invention include talc, kaolin, syloid.

The following examples are illustrative of the present invention.

EXAMPLE 1

Preparation of Coated Diphenhydramine HCl Micropellets

The core micropellets were prepared by layering an aqueous solution of diphenhydramine hydrochloride (DPH.HCl) containing a binder and antiadherent on lactose granules using a Wurster apparatus. Two hundred grams of lactose granules (Lactose Fast-Flo ®  74-150 µ) were charged into a fluid bed apparatus fitted with a Wurster column. The layering solution was sprayed on the fluidizing bed of lactose granules until the desired drug loading was achieved. The composition of the layering solution and process conditions are the following:

A. Layering Formulation for DPH.HCl
 DPH.HCl: 60 g
 Polyvinylpyrrolidone: 6 g
 Talc: 9 g
 Water, purified: 225 g B. Layering Conditions
 Spray rate: 0.5-1.5 ml/min
 Atomization air pressure: 2.4 bar
 Inlet temperature: 58°-60° C.
 Outlet temperature: 40° C.
 Fluidization air velocity: 12 M³/hour The micropellets were coated with cellulose as described below:

Surelease ®, an aqueous dispersion of ethylcellulose was diluted with water to a 15% w/w solids content and sprayed on the core micropellets using the Wurster apparatus. The coated micropellets were then overcoated with hydroxypropyl methylcellulose and the micropellets cured at 60° C. for 24 hours prior to packing into sachets each containing the equivalent of 25 mg of diphenhydramine.HCl.

EXAMPLE 2

Preparation of Procaterol Micropellets

Using the same equipment as mentioned under preparation of DPH.HCl micropellets, procaterol HCl micropellets were prepared by layering a buffered aqueous solution of procaterol HCl containing antiadherent and binder on lactose particles. The formula and processing conditions are set forth below.

A. Layering Formulation for Procaterol HCl Micropellets
   Procaterol HCl ½ $H_2O$: 0.924 g
   Citric acid: 0.176 g
   Sodium Citrate: 0.132 g
   Hydroxypropyl cellulose: 6.0 g
   Mistron talc: 4.0 g
   Water, purified to: 200.0 g B. Layering Conditions
   Spray rate: 0.5-2 ml/min
   Atomization air pressure: 1.6 bar
   Inlet temperature: 48° C.
   Outlet temperature: 29° C.
   Fluidization air velocity: 9-10 $M^3$/hour The coating of the core drug micropellets was carried out exactly as described in Example 1.

We claim:

1. A pharmaceutical preparation which is a coated drug micropellet comprising a sucrose or lactose core having diphenhydramine or procaterol layered thereon to form a drug micropellet to which is applied a coating of ethyl cellulose said coated drug micropellet being from about 70 microns to 150 microns in diameter.

2. A preparation of claim 1 wherein the drug micropellet has a hydroxypropylmethyl cellulose overcoating applied to the coating.

3. A preparation of claim 2 wherein the drug is diphenhydramine.

4. A preparation of claim 2 wherein the drug is procaterol.

* * * * *